(12) United States Patent
Kawano

(10) Patent No.: US 6,409,657 B1
(45) Date of Patent: Jun. 25, 2002

(54) CLEANING DEVICE FOR CLEANING VIEW WINDOW OF ENDOSCOPE

(75) Inventor: Hirotaka Kawano, Saitama (JP)

(73) Assignee: Fuji Photo Optical. Co., Ltd., Saitama (JP)

( * ) Notice: Subject to any disclaimer, the term of this patent is extended or adjusted under 35 U.S.C. 154(b) by 0 days.

(21) Appl. No.: 09/537,730

(22) Filed: Mar. 30, 2000

(30) Foreign Application Priority Data

Mar. 31, 1999 (JP) .............................. 11-091796

(51) Int. Cl.[7] ................................. A61B 1/12
(52) U.S. Cl. ................... 600/157; 600/158; 600/127
(58) Field of Search ................... 600/156, 157, 600/158, 159, 127, 129

(56) References Cited

U.S. PATENT DOCUMENTS

| | | | | |
|---|---|---|---|---|
| 5,131,382 A | * | 7/1992 | Meyer | 600/104 |
| 5,207,213 A | * | 5/1993 | Auhll et al. | 600/104 |
| 5,486,154 A | * | 1/1996 | Kelleher | 600/104 |
| 5,685,823 A | * | 11/1997 | Ito et al. | 600/127 |
| 5,725,476 A | * | 3/1998 | Yasui et al. | 600/127 |
| 5,725,477 A | * | 3/1998 | Yasui et al. | 600/127 |
| 5,733,243 A | * | 3/1998 | Yabe et al. | 600/121 |
| 5,935,097 A | * | 8/1999 | Metsch et al. | 604/27 |
| 5,944,654 A | * | 8/1999 | Crawford | 600/157 |
| 5,989,183 A | * | 11/1999 | Reisdorf et al. | 600/156 |
| 6,110,103 A | * | 8/2000 | Donofrio | 600/121 |
| 6,126,592 A | * | 10/2000 | Proch et al. | 600/114 |

* cited by examiner

Primary Examiner—Michael Peffley
Assistant Examiner—Jocelyn Ram
(74) Attorney, Agent, or Firm—Young & Thompson

(57) ABSTRACT

A viewing head cap that is made of an elastic material includes a cylindrical cap body and a spray nozzle formed integrally with the cap body and provides a drain port which is located at a location opposite to the spray nozzle with respect to a viewing window and opens between the cap body and a viewing head and which is communicated with a forceps channel functioning as a suction channel through a drain path.

10 Claims, 8 Drawing Sheets

CLEANING DEVICE FOR CLEANING VIEW WINDOW OF ENDOSCOPE

BACKGROUND OF THE INVENTION

1. Field of the Invention

The present invention relates to a medical endoscope equipped with a cleaning device for cleaning a viewing window of an insertion section.

2. Description of Related Art

A medical endoscope is generally made up of an insertion section including a bending section and a viewing head which is adapted for insertion into a human body cavity, an operating section connected to the viewing head through a flexible section and a light guide section through which the viewing head is connected to a light source unit. The viewing head, which is located right after the bending section, is provided with a viewing system comprising an illumination system for illuminating the inside of a human body cavity and an image pickup system including an imaging lens system for picking up a local image of the cavity interior under illumination. The illuminating system includes a light guide fiber bundle and an illumination lens system mounted, directly or through a protective glass plate, in an illumination window which is located immediately after a light exit end of the light guide fiber bundle. The image pickup system includes an image guide fiber bundle or a solid state imaging device such as a charge coupled device (CCD) and an objective or image forming lens system mounted, directly or through a protective glass plate, in an image viewing window adjacent to the illumination window for focusing an image of the interior of the human body cavity under illumination upon a light receiving surface of the light guide fiber bundle or the solid state imaging device.

When the viewing window gets dirty with body liquid which generally stagnates in a human body cavity into which the medical endoscope is inserted, the field of view of the endoscope gets dark and unclear. For this reason, the medical endoscope is typically provided with a structure for cleaning the viewing window in which the foremost lens element of the image forming lens system or the protective glass plate is located during observation and/or examination of a human body cavity. Cleaning the viewing window is implemented by injecting cleaning liquid or rinse water against the viewing window to wash dirt off and then blowing pressurized air against the viewing window. For the cleaning structure the endoscope is necessarily provided with an air feed channel and a water feed channel, both of which extend separately from the operating section to the distal end, or otherwise which extend separately halfway from the operating section and join into a common air/water feed channel to the distal end. In the medical endoscope provided with the air feed channel and the water feed channel incorporated separately all along the way or in the form of partly joined fashion, the cleaning liquid flows along an axial line of the viewing head and on the other hand, the image forming lens system is positioned in the viewing head with the optical axis placed perpendicularly to an extreme end plane of the viewing head, the air feed channel and the water feed channel have to turn at approximately 90° so as to direct the cleaning fluid toward the viewing window. On the grounds of the cleaning structure, the medical endoscope is typically equipped with a feeding nozzle at the extreme end of the viewing head. Usually, the feeding nozzle extends out of the extreme end of the viewing head and surrounds completely ports of the air feed channel and water feed channel or an outlet of the water/air feed channel. The feeding nozzle has a thin slot nozzle hole which is directed toward the lens element of the image forming lens system so as to force cleaning water/air to flow along the distal end of the viewing head. As is apparent, since the feeding nozzle works to cause a turnaround of a fluid flow and receives pressure from the fluid flow at the turning point, the nozzle has to be firmly secured to the viewing head, which is essential in order to prevent the feeding nozzle from coming off in the human body cavity.

Cleaning and sterilization of the medical endoscope after each observation and/or examination is essential in view of preventing secondary infection. For the same reason, cleaning and sterilization of the inside of the feed channel is also essential. Cleaning the air feed channel and the water feed channel may be done with a channel cleaning brush. However, in the case where the feed channel is provided with an feeding nozzle, there is the necessity of removing the feeding nozzle before inserting the channel cleaning brush into the air feed channel or the air feed channel, which is quit troublesome work.

There has been a medical endoscope that is equipped with a viewing head cap having a feeding nozzle integrally formed therewith. In addition to the requirement that the nozzle equipped viewing head cap is easily put on and off from the viewing head, there is the somewhat conflicting requirement that it is configured so as to be hard to come off from the viewing head during observation and/or examination. Further, it is required that the feeding nozzle direct fluid flow, in particular a pressurized flow, precisely toward the foremost lens surface of the image forming lens system or the protective glass plate. In compliance with these requirements, the viewing head is construed by a cylindrical rubber ring for surrounding the distal end section thereof and a spray nozzle which is made of a hard plastic for the reason of stable directivity of cleaning liquid sprayed from the nozzle. One of such endoscopes is known from, for example, Japanese Unexamined Patent Publication No. 8-140923. Some endoscopes, such as having been proposed in Japanese Utility Model Publication No. 6-41530, have plastic viewing head hoods. The hood has an integral feeding nozzle that is located in a position opposite to a suction opening with respect to a viewing window so as to cover an opening of a fluid feed channel and injects cleaning fluid toward the viewing window. The hood is formed with a groove extending from the feeding nozzle to the suction opening through which cleaning fluid injected by the feeding nozzle is sucked into a suction channel. This hood provides reliable injection of cleaning liquid over the viewing window and reliable suction of the cleaning liquid. The viewing head cap or the viewing head hood that is formed integrally with a feeding nozzle and detachably put on the viewing head makes it easy to wash and clean the cleaning liquid feed channel.

The nozzle equipped viewing head cap that has been disclosed in Japanese Unexamined Patent Publication No. 8-140923 can provide a stable nozzle configuration which is desirable for directing a stream of cleaning liquid accurately toward the viewing window and washing the viewing window effectively, and is easily and reliably put on the viewing head. However, the nozzle equipped viewing head cap has to be prepared by integrating two pieces made of materials different in quality, so as to be inferior in terms of productivity and production costs. On the other hand, while the nozzle equipped viewing head hood that has been disclosed in Japanese Utility Model Publication No. 6-41530 can provide an enhanced effect of cleaning the viewing window and, in particular, effective removal of water drops from the viewing window because of suction of cleaning liquid through the suction opening, however, the nozzle equipped viewing head hood has a necessity of arranging the feeding nozzle so as to be on a straight line crossing the viewing window and the suction opening, which imposes restraints on the lay-out of necessary parts and elements of the viewing head, it is difficult to make the insertion section slender.

SUMMARY OF THE INVENTION

It is therefore an object of the present invention to provide a medical endoscope that makes the structure of a feeding nozzle simple and is possible to wash dirt and liquid drops off from a viewing window without being affected by the arrangement of various related parts and elements of a viewing head.

The above object is accomplished by a medical endoscope having an insertion section including a viewing head which is connected to an operating section through a flexible section and includes an illumination system located behind an illumination window, a viewing lens system located behind a viewing window, fluid feed means through which at least cleaning fluid is fed to the viewing window, and suction feed means through which suction is applied to a distal end of the viewing head, which comprises a cylindrical viewing head casing for housing the illumination system, the viewing lens system, and the fluid feed means therein; an annular-shaped viewing head cap detachably fitted to the generally cylindrical viewing head casing, the viewing head cap being formed so as to have an generally cylindrical wall extending a predetermined height from a distal end of the viewing head casing in a lengthwise direction of the insertion section, a fluid feeding nozzle having an injection port through which the cleaning fluid fed through the fluid feed means is injected, the fluid feeding nozzle being formed integrally with the generally annular-shaped viewing head cap and configured to form a fluid path which is brought into communication with the fluid feed means when the generally annular-shaped viewing head cap is fitted to the generally cylindrical viewing head casing and turn to direct the cleaning fluid through the fluid feed means toward the viewing window; and a drain path opening to a space formed between the cylindrical wall of the generally annular-shaped viewing head cap and the distal end of the viewing head at one of opposite ends thereof and being in communication with the suction feed means at another of the opposite ends so that liquid that stays in the space is sucked through the drain path into the suction feed means. Specifically, the drain path comprises a drain port having a predetermined opening angle at a location opposite to the injection port of the fluid feeding nozzle, a drain ditch which is formed between a groove formed in the generally cylindrical wall of the generally annular-shaped viewing head cap and the generally cylindrical viewing head casing so as to be in communication with the drain port, and a communication path through which the drain path is communicated with the suction feed means.

The fluid feed means may comprise a cleaning water feed channel and an air feed channel separately extending from the viewing head to the operating section, or otherwise, the fluid feed means may comprise a cleaning water feed channel and an air feed channel separately extending in the insertion section and joining together in the flexible section. In terms of easy cleaning, the medical endoscope is preferred to have no diverging section in the fluid feed means.

The viewing head casing may be formed with a recess in its distal end so that the fluid feed means, more specifically the cleaning water feed channel and the air feed channel opens in the recess and the fluid feeding nozzle is fitted in the recess.

The drain port is preferably configured so as to extend in conformity with or covering a spread angle of fluid injected by the fluid feeding nozzle.

BRIEF DESCRIPTION OF THE DRAWINGS

The above and other objects and features will be more clearly understood from the following description in regards to the preferred embodiment thereof when reading in conjunction with the accompanying drawings, in which.

DETAILED DESCRIPTION OF THE PREFERRED EMBODIMENT

Figure 1:
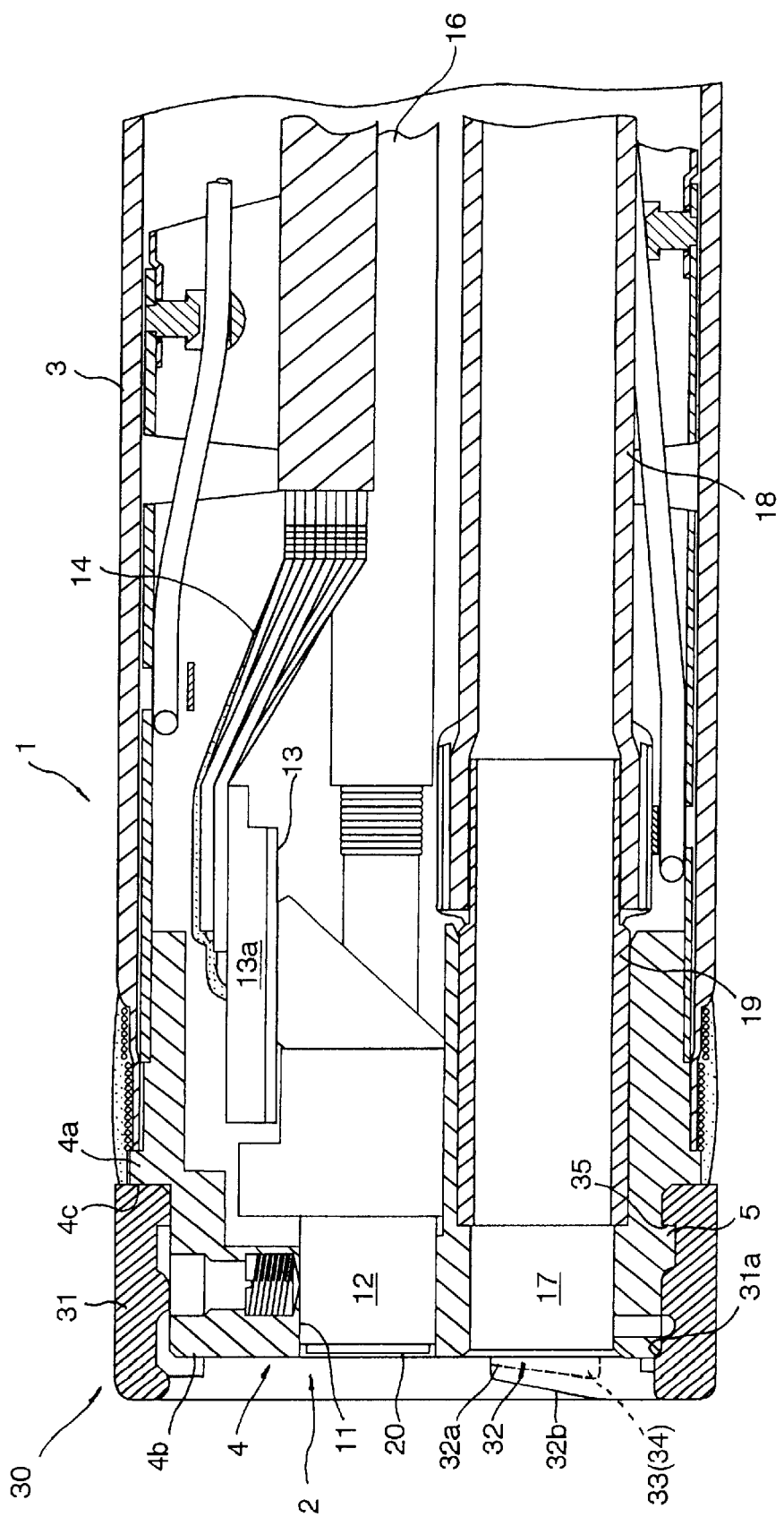
FIG. 1 is a cross sectional view showing a viewing head of a medical endoscope in accordance with a preferred embodiment of the present invention.
Figure 2:
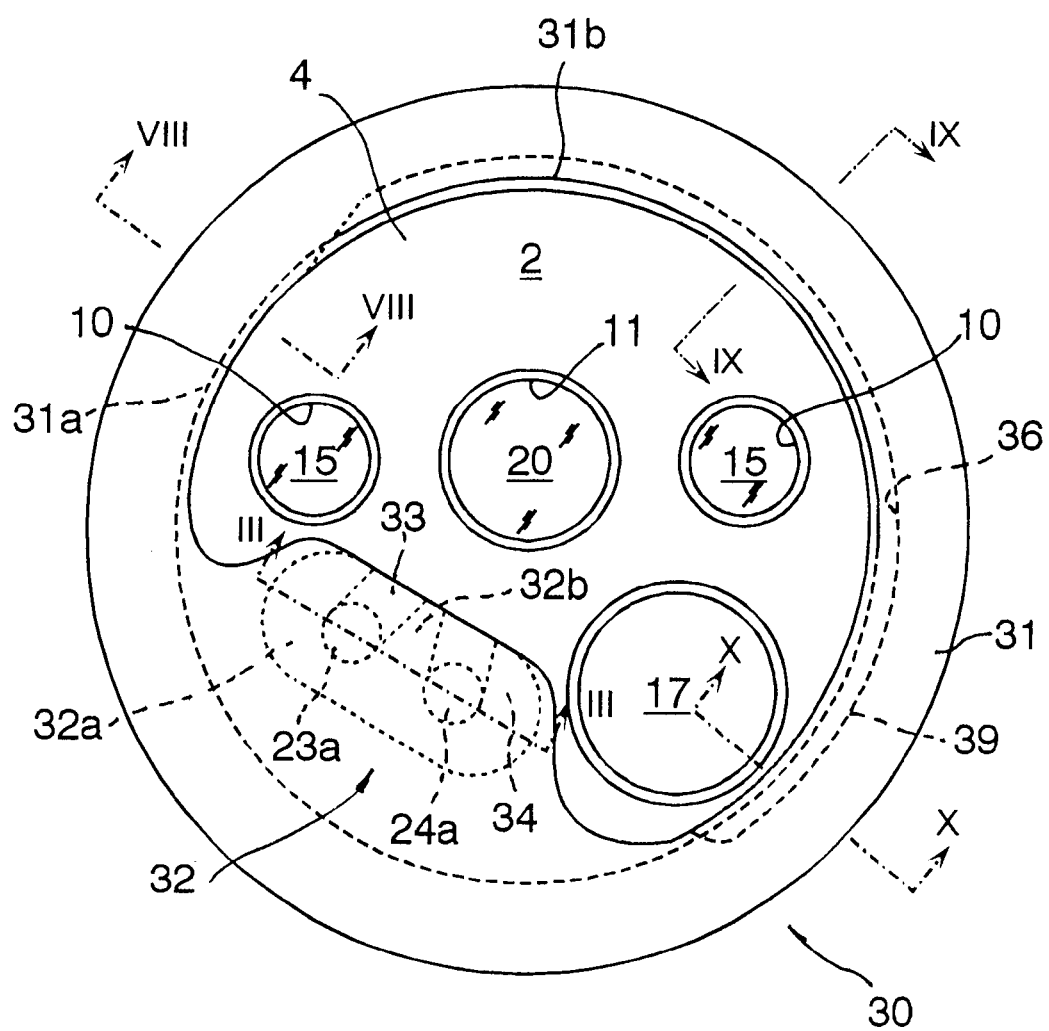
FIG. 2 is an external view showing a front end of the viewing head.

Referring to the drawings in detail, and, in particular, to FIGS. 1 and 2 which shows an insertion section 1 which forms a distal end section of a medical endoscope (not show) in accordance with the present invention, the insertion section 1 includes a viewing head 2 and a bending section 3 to which the viewing head 2 is joined. The bending section 3 is bent in desired directions through remote control at an operating section of the medical endoscope. The viewing head 2 has a substantially cylindrical casing 4 made of a metal or hard plastics which have superior workability and high strength. This viewing head casing 4 is formed a plurality of bores into which various parts are inserted. As shown in FIG. 2, the viewing head 2 at its distal end is formed with a viewing window 11 and a pair of illumination windows 10 that are located symmetrically with respect to the viewing window 11. The viewing window 11 is preferred to be located at the center of the viewing head 2.

A lens barrel 12 in which an image forming lens system (not shown) is installed is fitted in the viewing window 11. The image forming lens system is arranged to focus an image of an aimed scene contained in an object plane thereof upon a light receiving surface of a self-scanning solid state imaging device 13 such as a charge coupled device (CCD) mounted on a base plate 13a. Read-out lines 14 are connected to the solid state imaging device 13 to transmit visual information signal from the solid state imaging device 13 to an external viewing equipment (not shown) such as television equipment and video processing equipment. An illumination lens system 15 is fitted in each illumination window 10 so as to face to a light exit end of a guide fiber bundle 16.

The viewing head 1 is further formed with a forceps window 17 that is in connection with a forceps channel 18 through a connecting pipe 19. A forceps such as a biopsy forceps, a polypectomy forceps and the like is inserted into a human body cavity under observation and/or examination through the forceps channel 18 and projected through the forceps window 17 for biopsy, polypectomy and the like. The forceps channel 18 is also used as a suction channel through which body liquid is sucked by an external suction pump.

A protective glass plate or a foremost lens element of the image forming lens system (which is hereafter referred to as a viewing window optical element 20) fitted directly in the viewing window 11 is always exposed to surroundings dirtied by body liquid and the like and has a great chance to be dirty with the result of loosing a clear view. For preventing the view window optical element 20 from getting too dirty to provide a clear view, the medical endoscope is equipped with a viewing window cleaning device for cleaning the viewing window optical element 20 by injecting cleaning water against the viewing window optical element 20 so as to wash dirt off from the viewing window optical element 20 and subsequently blowing pressurized air so as to remove water drops away from the viewing window optical element 20.

Figure 3:
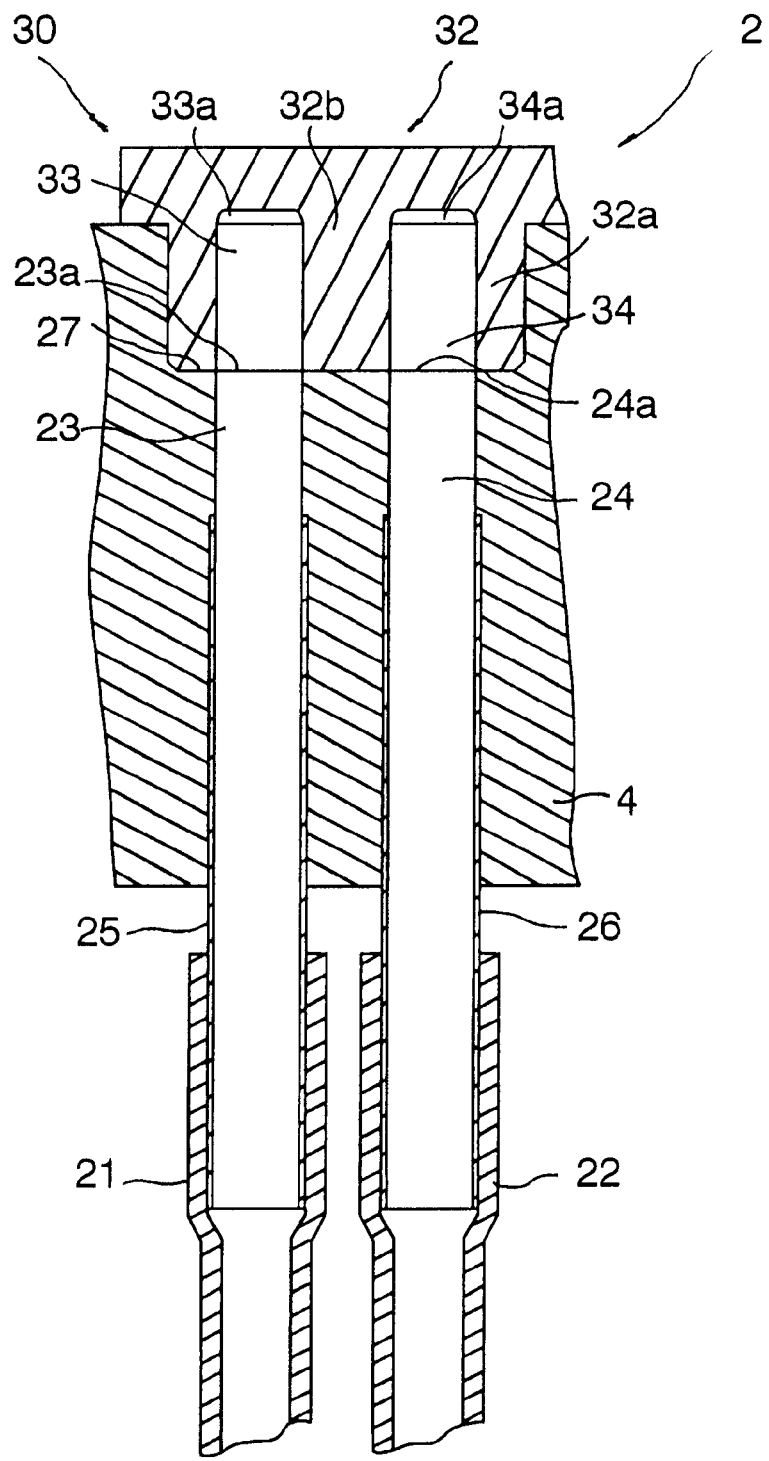
FIG. 3 is a cross sectional-view of FIG. 2 taken along line III—III.
Figure 4:
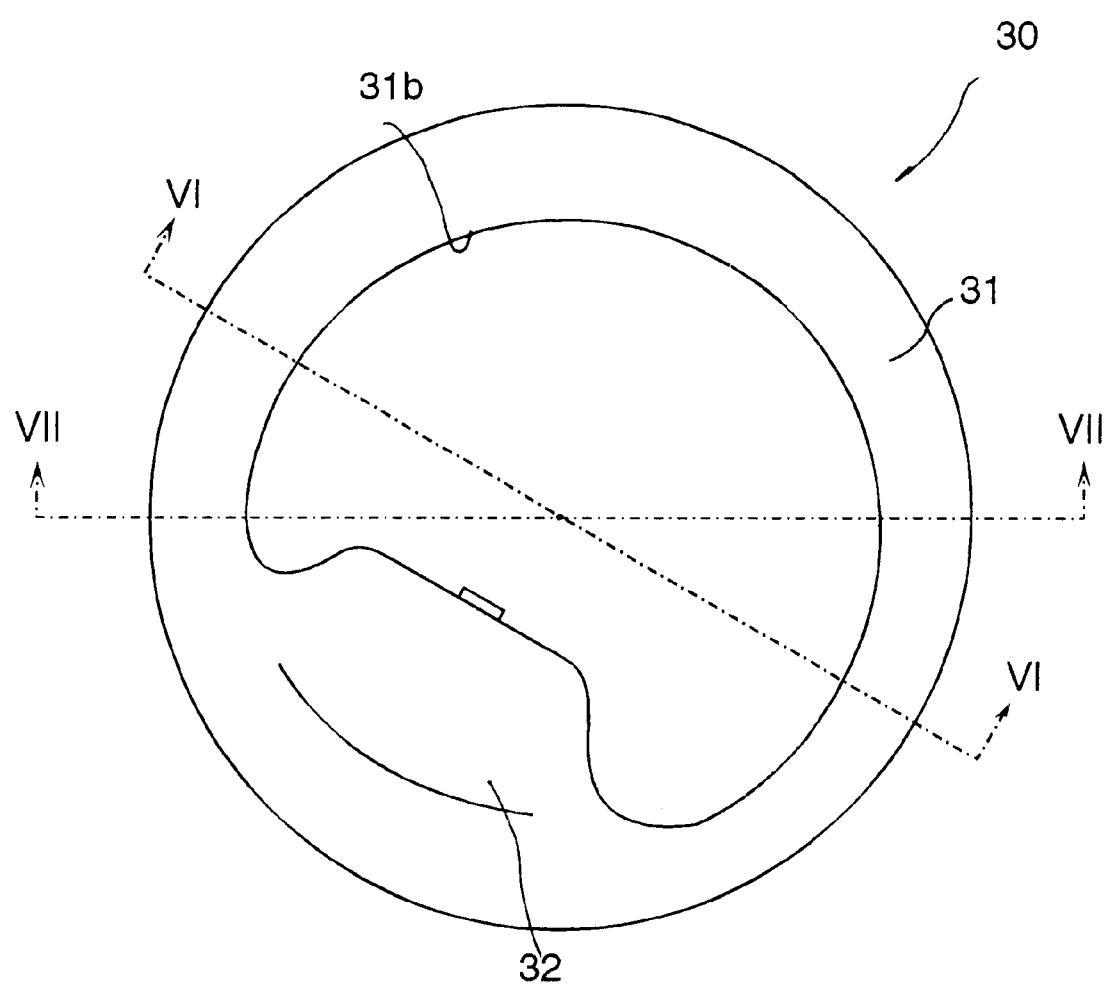
FIG. 4 is a plane view showing a viewing head cap.

Referring to FIG. 3 showing the viewing window cleaning device, the cylindrical viewing head casing 4 is formed with a water feed channel 23 and an air feed channel 24 which are arranged side by side and extend in an axial direction of the viewing head casing 4. Connection pipes 25 and 26 are fixedly inserted in the water feed channel 23 and the air feed channel 24, respectively. A water feed tube 21 and an air feed tube 22 are connected to the water feed channel 23 and the air feed channel 24, respectively, through the connecting pipes 25 and 26, respectively. These water feed tube 21 and air feed tube 22 extend inside the medical endoscope all the way long and are connected to a water/air supply unit (not shown) that is prepared as an external equipment through a water supply valve and an air supply valve provided in the operating section, respectively. The water feed channel 23 has a water feed port 23a opening to a nozzle mounting recess 27 at the distal end of the viewing head casing 4. Similarly, the air feed channel 24 has an air feed port 24a opening to the nozzle mounting recess 27 of the viewing head housing 4. An generally annular-shaped viewing head cap 30 such as shown in FIG. 4 is detachably put on the distal end of the viewing head housing 4. As clearly seen in FIG. 1, the viewing head cap 30, which is made of an elastic material such as rubber, has a generally cylindrical wall 31 and a feeding nozzle 32 which are formed integrally as one whole.

Figure 5:
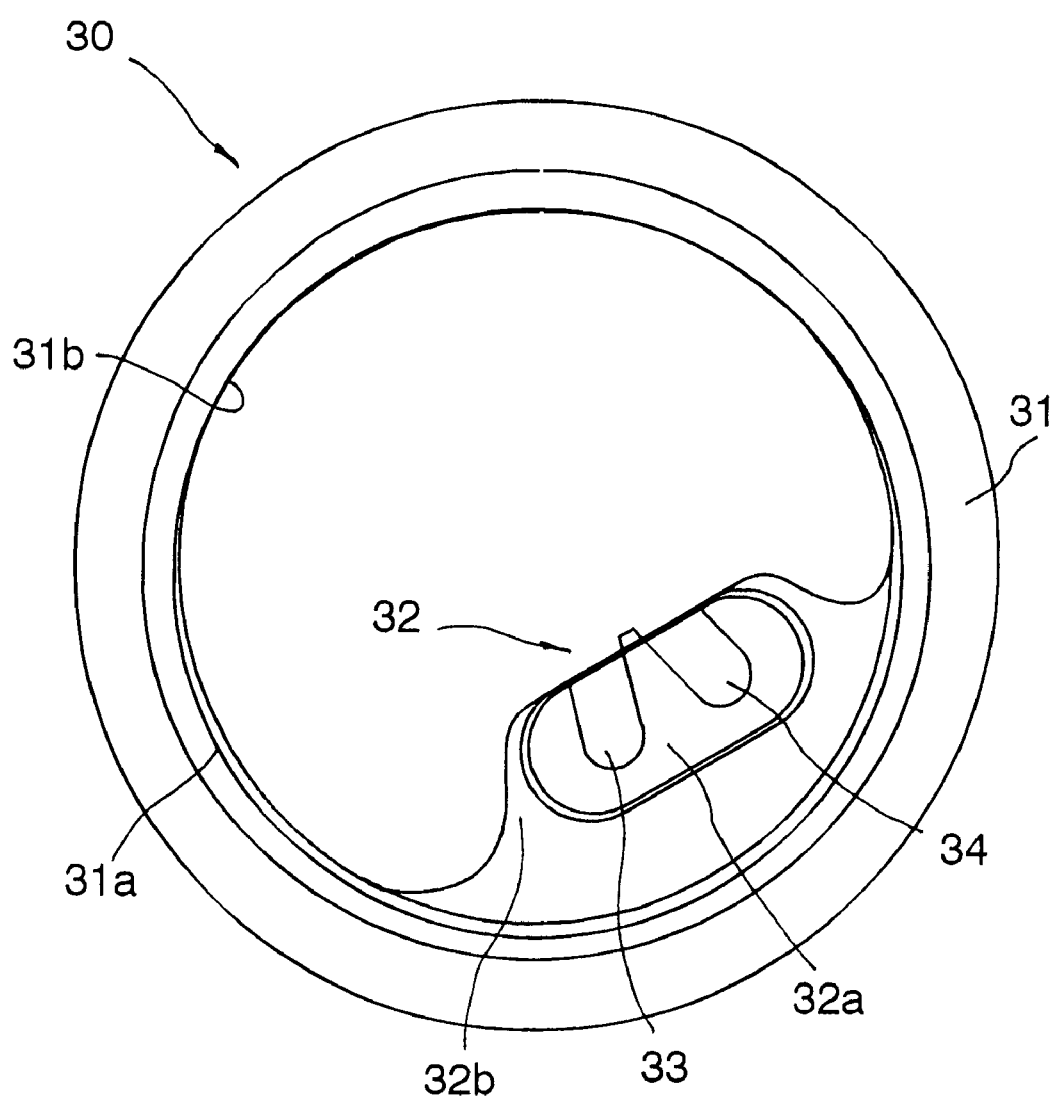
FIG. 5 is a bottom view of the viewing head cap.
Figure 6:
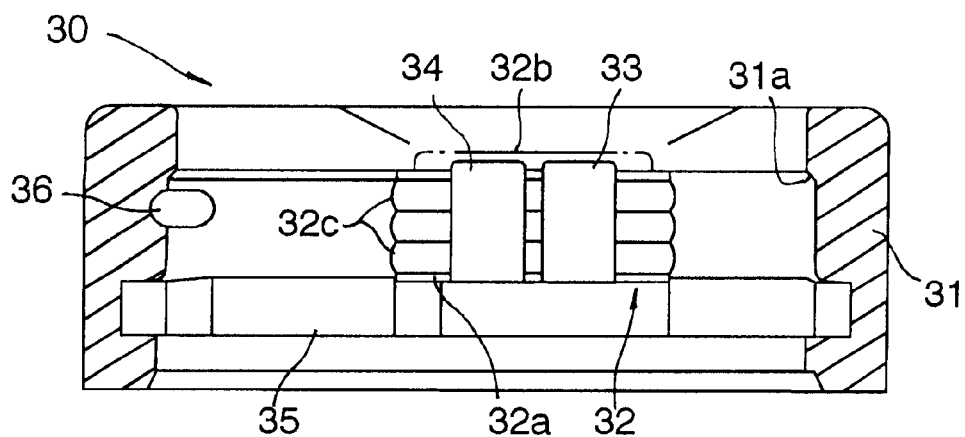
FIG. 6 is a cross-sectional view of FIG. 4 taken along line VI—VI.
Figure 7:
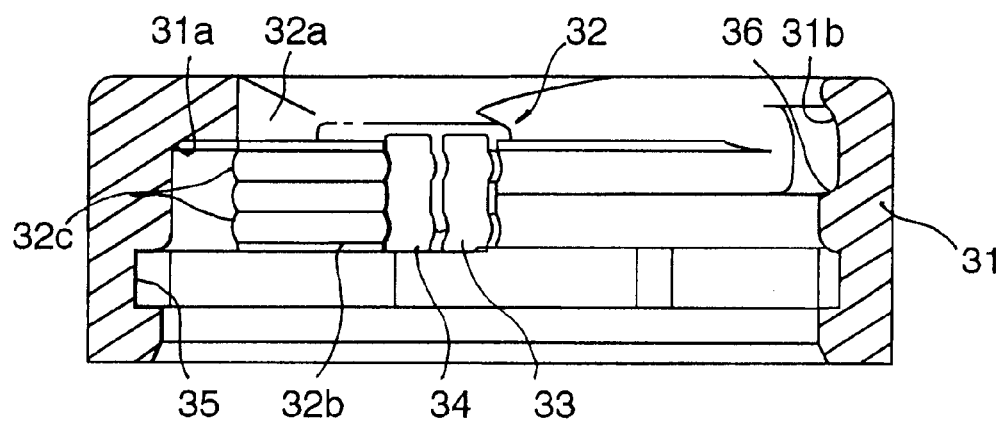
FIG. 7 is a cross-sectional view of FIG. 4 taken along line VII—VII.

As shown in FIGS. 4 to 7, the cylindrical wall 31 is configured to fit on the shoulder 4c at the distal end of the viewing head housing 4 and has a specified wall height so as to extend forward by a specified axial distance from a plane containing the viewing window optical element 20. The feeding nozzle 32 has a nozzle body 32a extending in parallel with the cylindrical wall 31 of the viewing head cap 30 but having a height shorter than the cylindrical wall 31 of the viewing head cap 30 as shown in FIG. 6 and a top wall 32b extending radially over a specified angle from the top of the cylindrical wall 31 as shown in FIG. 5. The nozzle body 32a is formed with a pair of grooves which extends initially along the inner wall of the nozzle body 32a and then along the top wall 32b of the nozzle body 32a so as to open at an inner edge of the top wall 32b and upper and lower projections 32c at the outer wall thereof. The nozzle body 32a thus configured is fitted and firmly situated in the nozzle mounting recess 27 at the distal end of the viewing head casing 4 with the upper and lower projections 32c in engagement with the inner wall of the nozzlmounting recess 27 when the viewing head cap 30 is put on the distal end of the viewing head housing 4. The grooves extending between the inner wall and top wall 32b of the nozzle body 32a form fluid channels 33 and 34 between the inner wall of the nozzle mounting recess 27 and the distal end of the viewing head casing 4 while the viewing head cap 30 remains on the distal end of the viewing head housing 4. As apparent, each of the fluid channels 33 and 34 form a turnaround of the path of fluid flow at approximately 900 or an angle slightly less than 90° at a transitional corner from the inner wall to the top wall 32b of the nozzle body 32a. The water feed channel 23 leads to the fluid channel 33 and the end of the fluid channel 33 that opens at the inner edge of the top wall 32b forms a water injection port 33a. The air feed channel 24 leads to the fluid channel 34 and the end of the fluid channel 34 that opens at the inner edge of the top wall 32b forms an air injection port 34aThese ports 33a and 34a are shaped in the form of slit that is and located as close to the viewing window 11 as possible and directed toward to the viewing window 11. In order for the feeding nozzle 32 to be located as close to the viewing window 11 as possible, the outer surface of the top wall 32b of the feeding nozzle 32 is lower in level at the side where the spray ports 33a and 34a are formed and sloped up toward the side remote from the viewing window 11.

The viewing head cap 30 put on the viewing head 2 extends forward from the extreme end of the viewing head 2 by a specified distance and is adapted, on one hand, to be easily taken off and, on the other hand, to be held steady so as to be prevented from easily coming off. For this structure, the viewing head casing 4 is comprised of two parts, namely a large diameter cylindrical casing section 4a on the side of the bending section 3 and a small diameter cylindrical casing section 4b on the side remote from the bending section 3. The shoulder 4c which the cylindrical wall 31 fits on is formed between the larger and smaller diameter casing sections 4a and 4b. For evenness of the external surface of the insertion section 1 over the viewing head 4 and the viewing head cap 30 put on the viewing head 4, the viewing head cap 30, and hence the cylindrical wall 31, has an external diameter approximately equal to that of the larger diameter casing sections 4a. The smaller diameter casing section 4b is formed with a plurality of, for example four in this embodiment, radial projections 5 as shown in FIG. 1 and the viewing head cap 30 is formed with an internal annular groove 35 in the cylindrical wall 31 for engagement with the radial projections 5 of the smaller diameter casing section 4b. By means of this engagement, the viewing head cap 30 is firmly held by the viewing head casing 4 during observation and/or examination. As was previously described, the cylindrical wall 31 has the wall height so as to extend forward by a specified axial distance from the plane containing the viewing window optical element 20. The extension at its distal edge is formed with a swelling 31a over an angle sufficient to cover the feeding nozzle 32. The swelling 31a is brought into tight contact to the front edge of the small diameter casing section 4b where the feeding nozzle, 32 is provided. Further the cylindrical wall 31 is formed with a depression 31b in a position opposite to the swelling 31a. The cylindrical wall 31 is accordingly separated away from both front and side wall of the distal end of the viewing head casing 4 by specified distances. Furthermore the viewing head cap 30 is formed with a circular arcuate groove 36 having a specified extent on the cylindrical wall 31 between the internal annular groove 35 and the swelling 31a. This circular arcuate groove 36 partly overlaps the depression 31b.

Figure 8:
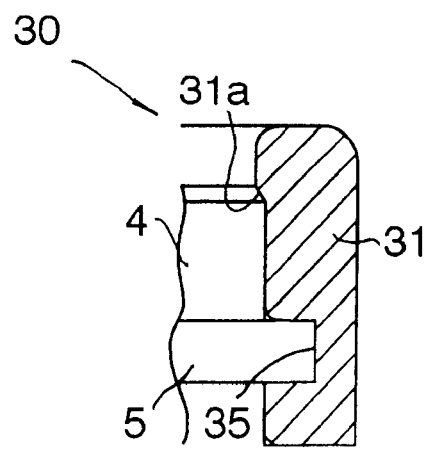
FIG. 8 is a cross-sectional view of FIG. 2 taken along line VIII—VIII.
Figure 9:
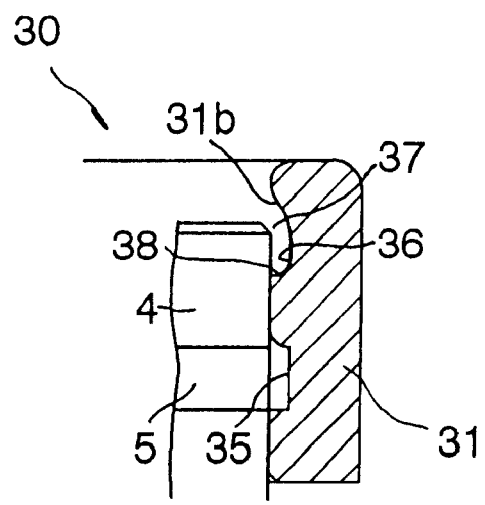
FIG. 9 is a cross-sectional view of FIG. 2 taken along line IX—IX.
Figure 10:
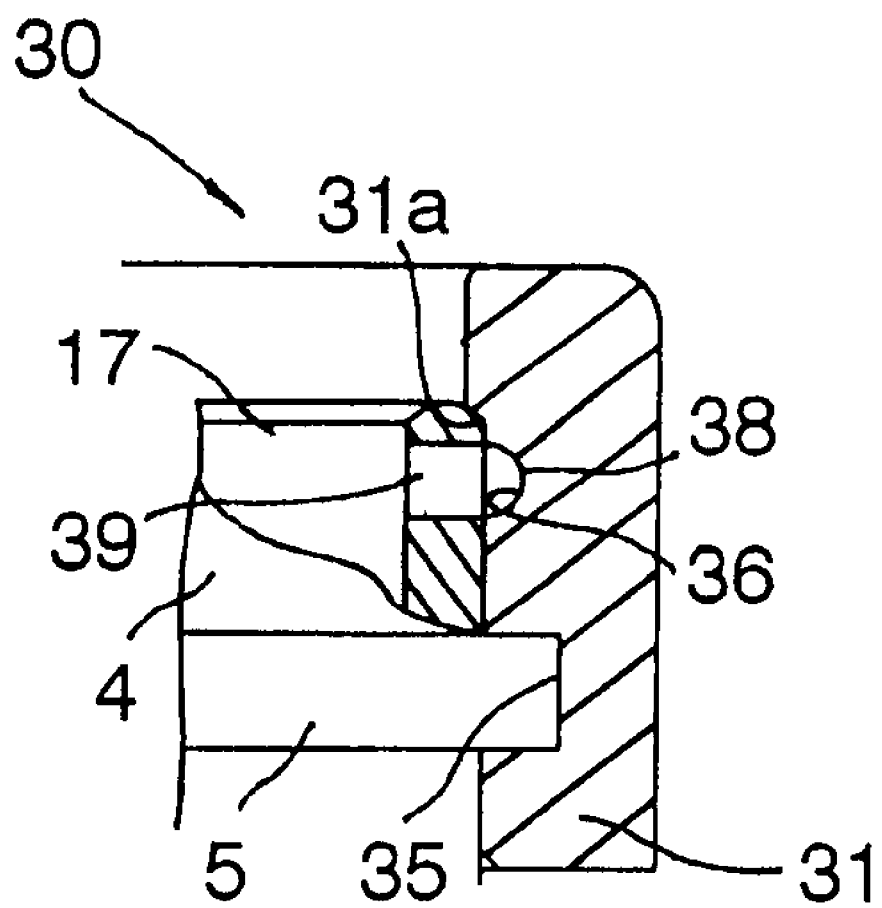
FIG. 10 is a cross-sectional view of FIG. 2 taken along line X—X.

The cylindrical wall 31 of the viewing head cap 30 forms a circumferential wall for encircling the entire circumference of an end portion of the viewing head casing 4 and tightly contacts with the viewing head casing 4 through a specified portion including the swelling 31a as shown in FIG. 8. Between the viewing head casing 4 and the viewing head cap 30 there is provided a drain port 37 defined by the depression 31b that is located oppositely to the feeding nozzle 32 and a drain ditch 38 which is formed by the circular arcuate groove 36 and in communication with the drain port 37 as shown in FIG. 9. The drain ditch 38 is formed as a tunnel starting from the drain port 37. The viewing head casing 4 is formed with a communication path 39 on the outer wall. This communication path 39 is in communication with the forceps window 17. Accordingly, the viewing head casing 4 has a drain path which extends from the drain port 37 located oppositely to the feeding nozzle 32 to the forceps window 17 through the drain ditch 38 extending on the outer wall of the cylindrical wall 31 of the viewing head cap 30 and the communication path 39. In the case where an independent suction channel is provided in the viewing head 2, the communication path 39 is opened to the independent suction channel.

When the window optical element 20 in the viewing window 11 gets dirty with body liquid and the like while the insertion section 1 stays in a human body cavity for observation and/or examination, the water supply valve is operated at the operating section to feed water to the feeding nozzle 32 through the water feed channel 23. Specifically, the cleaning water flow travels into the fluid channel 33 of the feeding nozzle 32 passing through the water feed tube 21 and then the water feed channel 23. The cleaning water flow turns at approximately 90° and is directed inward during traveling through the fluid channel 33. The feeding nozzle 32 injects the cleaning water with a specified level of pressure through the water injection port 33a against the window optical element 20. As a result, the cleaning water flows on the window optical element 20 in the viewing window 11 to wash body liquid and dirty off. Subsequently, after interrupting supply of cleaning water, the air supply valve is operated at the operating section to feed pressurized air to the feeding nozzle 34 through the air feed channel 24 and the air feed tube 22 and injects the pressurized air against the window optical element 20 through the air injection port 34a of the feeding nozzle 34, so as to blow off water drops on the window optical element 20 in the viewing window 11 and dries it. After interrupting air supply, observation and/or examination of a human body cavity is resumed. In this instance, although the water injection port 33a and the air injection port 34a are directed toward the viewing window 11, since the viewing head cap 30 including these injection ports 33a and 34a is configured to be somewhat expandable in consideration of easiness to put on and off, the injection ports 33a and 34a does not always keep their port shapes. The cleaning water injected from the water injection port 33a springs spreading on both sides, so that the cleaning water washes over the window optical elements 20 and washes dirty off even if the injection ports 33a and 34a change their port shape. However, it is not always left trustworthy that the pressurized air simply blows over the window optical element 20, and it is always required that the pressurized air applies blast pressure sufficiently high to sweep water drops on the window optical element 20. Some shapes of the air injection port 34a is sometimes hard to apply sufficiently high blast pressure against the window optical element 20 only by pressurize the air more highly. On the grounds of the necessity of applying sufficiently high pressure against the window optical element 20, the forceps channel 18 is connected to an external suction supply installed in the clinical site upon injecting pressurized air through the air injection port 34a at the latest or, preferably, immediately after injecting cleaning water through the water injection port 33a. In this instance, since the forceps channel 18 is in communication with the drain port 37 through the drain ditch 38 and the communication path 39, suction acts on at the distal end of the viewing head 2 through the drain port 37. Further, since the drain port 37 is located oppositely to the air injection port 34a, the pressurized air from the air injection port 34a gets to be intensified with respect to the negative pressure produced at the drain port 37, as a result of which the pressurized air rushes on the window optical element 20, so that water drops on the window optical element 20 are blown off with the pressurized air and the suction and reliably removed off therefrom. Moreover, liquid including body liquid and cleaning water staying between the inside of the extension of the cylindrical wall 31 of the viewing head cap 30 and the distal end of the viewing head casing 4 is removed by the suction. Accordingly, the distal end of the viewing head 2 is kept from dirty and liquid, so as thereby to prevent the window optical element 20 from getting so dirty to deteriorate view of the image forming lens system. Once the window optical element 20 is cleaned of dirt, it is prevented from getting dirty again during observation and/or examination in one try.

Usually, for the purpose of maintenance and sterilization, the medical endoscope, in particular the insertion section of the medical endoscope, is well washed in running water and wiped with gauze soaked in alcohol. Before cleaning the medical endoscope, the viewing head cap 30 is removed from the viewing head casing 4 and cleaned in the same manner. The viewing head cap 30 is made entirely of an elastic material. Accordingly pulling the viewing head cap 30 from the viewing head casing 4 causes distortion and expansion of the viewing head cap 30, especially, at the annular groove 35, so as to bring the four radial projections 5 of the small diameter cylindrical casing section 4b of the viewing head casing 4 into disengagement with the annular groove 35, so as to put off from the viewing head casing 4. When the medical endoscope is intended to use, the viewing head cap 30 is attached to the viewing head casing 4 by pulling the viewing head cap 30 against the small diameter cylindrical casing section 4b of the viewing head casing 4. Pulling the viewing head cap 30 against the small diameter cylindrical casing section 4b causes partial distortion and partial expansion of the viewing head cap 30 and brings the annular groove 35 into engagement with the radial projections 5, so as thereby to easily and firmly put the viewing head cap 30 on the small diameter cylindrical casing section 4b of the viewing head casing 4. At this time, the viewing head cap 30 is positioned so as to place the nozzle body 32a of the feeding nozzle 32 in the nozzle mounting recess 27 of the viewing head casing 4, which directs precisely the feeding nozzle 32 toward the viewing window 11 with the result of precisely directing both water injection port 33a and air injection port 34a toward the window optical element 20 on opposite sides of the viewing window 11.

The viewing head cap 30 having the water/air feeding nozzle 32 that are made of an elastic material as an integral body and configured so as to be put on and off from the viewing head casing 4 is cheap, which is always desirable when the part is to be disposable. When putting the viewing head cap 30 off from the viewing head casing 4, the water/air spray valve 32 is removed from the water and air feed channels 23 and 24 concurrently, so that washing and cleaning the water and air feed channels 23 and 24 is quite easy. Although the water/air feeding nozzle 32 is elastic and in consequence distortable, because suction is applied to a location opposite to the feeding nozzle 32 with respect to the viewing window 11 so as to reliably direct cleaning fluid to the window optical element 20 in the viewing window 11 and, in particular, pressurized air is so intensified as to blow water drops off from the window optical element 20, washing and cleaning of the window optical element 20 is reliable and perfect. Moreover, the forceps channel 18 that is used as a suction channel is in communication with the drain port 37 through the drain ditch 38 and the communication path 39 and, besides, the drain ditch 38 is formed so as to surround partly the outer periphery of the viewing head casing 4, so that the location of the forceps window 17 does not impose any restraint on arrangement of the water/air feeding nozzle 32 and the viewing window 11. In consequence, the forceps window 17 can be laid at a location which is the best in terms of making the insertion section 1 slender and convenient handling of forceps.

What is claimed is:

1. A medical endoscope having an insertion section including a viewing head which is connected to an operating section through a flexible section and includes an illumination system located behind an illumination window, a viewing lens system located behind a viewing window, fluid feed means for feeding at least cleaning fluid to the viewing window, and suction feed means for feeding suction to the viewing head, said medical endoscope comprising:

a generally cylindrical viewing head casing for housing said illumination system, said viewing lens system and said fluid feed means therein;

a generally annular-shaped viewing head cap detachably fitted to said generally cylindrical viewing head casing, said viewing head cap being formed so as to have a generally cylindrical wall extending a predetermined height from a distal end of said viewing head casing in a lengthwise direction of said insertion section;

a fluid feeding nozzle having a fluid injection port through which said cleaning fluid can be fed, said fluid feeding nozzle being formed integrally with said generally annular-shaped viewing head cap and configured to form a fluid path which is brought into communication with said fluid feed means when said generally annular-shaped viewing head cap is fitted to said generally cylindrical viewing head casing and is turned to direct said cleaning fluid through said fluid feed means toward said viewing window; and a drain path opening to a space formed between said cylindrical wall of said generally annular-shaped viewing head cap and said distal end of said viewing head at a distal end and being in communication with said suction feed means a proximal end so that liquid that stays in said space is sucked through said drain path into said suction feed means.

2. A medical endoscope as defined in claim 1, wherein said drain path comprises a drain port having a predetermined opening angle at a location opposite to said injection port of said fluid feeding nozzle, a drain ditch which is formed between a groove formed in said generally cylindrical wall of said generally annular-shaped viewing head cap and said generally cylindrical viewing head casing so as to be in communication with said drain port, and a communication path through which said drain path is communicated with said suction feed means.

3. A medical endoscope as defined in claim 2, and further comprising a recess formed in an distal end of said generally cylindrical viewing head casing, wherein said fluid feed means opens in said recess and said fluid feeding nozzle is fitted in said recess.

4. A medical endoscope as defined in claim 3, wherein said fluid feed means comprises a cleaning liquid feed channel and an air feed channel and said fluid feeding nozzle has a cleaning liquid injection port and an air injection port.

5. A medical endoscope as defined in claim 2, wherein said drain port is defined by a depression located oppositely to said fluid feeding nozzle.

6. A medical endoscope as defined in claim 2, wherein said generally annular-shaped viewing head cap is made of an elastic material.

7. A medical endoscope as defined in claim 2, and further comprising stopper means which comprises a plurality of radial projections extending outward from said generally cylindrical viewing head casing and an annular groove formed in said cylindrical wall of said generally annular-shaped viewing head cap for receiving said radial projections.

8. A medical endoscope as defined in claim 2, wherein said fluid feed means comprises a cleaning water feed channel and an air feed channel separately extending from said viewing head to said operating section.

9. A medical endoscope as defined in claim 2, wherein said fluid feed means comprises a cleaning water feed channel and an air feed channel separately extending in said insertion section and joining together in said flexible section.

10. A medical endoscope as defined in claim 2, wherein said suction feed means comprise a forceps channel.

* * * * *